(12) United States Patent
Van Soolingen et al.

(10) Patent No.: US 6,326,521 B2
(45) Date of Patent: *Dec. 4, 2001

(54) PROCESS FOR THE PREPARATION OF BENZYL ALCOHOL

(75) Inventors: Jacob Van Soolingen, Brunssum; Alexander P. M. Vrinzen, Meerssen; Christiaan J. C. Stoelwinder, Sittard; Abram Peet, Maassluis; Hendricus J. Rozie, Born; Otto G. Plantema, Nederweert, all of (NL)

(73) Assignee: DSM N.V., Heerlen (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/215,244

(22) Filed: Dec. 18, 1998

(51) Int. Cl.$^7$ ..................................................... C07C 33/18
(52) U.S. Cl. ............................................ 568/715; 568/810
(58) Field of Search ..................................... 568/715, 810

(56) References Cited

U.S. PATENT DOCUMENTS

| | | | |
|---|---|---|---|
| 4,088,823 | 5/1978 | Holtz . | |
| 4,205,184 | * 5/1980 | Jongsma | ................. 562/494 |
| 4,227,017 | * 10/1980 | Jongsma | ................. 562/494 |
| 4,250,344 | * 2/1981 | Sherwin | ................. 585/437 |
| 4,281,178 | * 7/1981 | Sidi | ................. 562/412 |
| 4,283,565 | * 8/1981 | Bernhardt | ................. 568/648 |
| 4,296,245 | 10/1981 | Jongsma . | |
| 5,338,442 | * 8/1994 | Siskin | ................. 208/435 |

FOREIGN PATENT DOCUMENTS

| | | | |
|---|---|---|---|
| 2758487 | * 6/1978 | (DE) . | |
| 778257 | 6/1997 | (EP) . | |
| 1570858 | * 7/1980 | (GB) . | |

OTHER PUBLICATIONS

Tsao, J. Spuercrit. Fluids, vol. 5, pp. 107–113, 1992.*

* cited by examiner

Primary Examiner—Michael L. Shippen
(74) Attorney, Agent, or Firm—Pillsbury Winthrop LLP

(57) ABSTRACT

Process for the preparation of benzyl alcohol via hydrolysis of a benzyl ester with water in the liquid phase, the hydrolysis being carried out in the absence of a strong acid and a base at a temperature between 40° C. and 320° C. The benzyl ester to be hydrolyzed can be chosen from the group comprising benzyl formate, benzyl propionate, benzyl acetate and benzyl benzoate. A weak acid may optionally be added to the reaction mixture to be hydrolyzed. After the hydrolysis the reaction mixture is preferably cooled to a temperature between 80° C. and 180° C. so that a phase separation takes place. Both the organic phase and the aqueous phase can be upgraded. As such, benzyl alcohol can be obtained with a high overall yield and a purity of more than 98%.

15 Claims, No Drawings

PROCESS FOR THE PREPARATION OF BENZYL ALCOHOL

BACKGROUND OF THE INVENTION

1. Field of the Invention

The invention relates to a process for the preparation of benzyl alcohol via hydrolysis of a benzyl ester with water in the liquid phase.

2. Description of the Related Art

NL-A-7614458 describes a process for processing a tar containing benzyl benzoate via a hydrolysis reaction in the liquid phase. The hydrolysis can be carried out in the presence of a strong acid, for example a mineral acid such as sulphuric acid or phosphoric acid, or in the presence of a basic solution, in particular an aqueous sodium hydroxide or soda solution. Both embodiments present the drawback that the reaction mixture has to be neutralized afterwards so that salts are formed. The processing and disposal of salts are not desirable from an economic and an environmental viewpoint. The use of a strong acid moreover presents the drawback that it is highly corrosive and as such imposes high demands on the material of the equipment.

DETAILED DESCRIPTION OF THE INVENTION

The aim of the present invention is to solve the aforementioned drawbacks.

This aim is achieved according to the invention by carrying out the hydrolysis of a benzyl ester with water in the liquid phase in the absence of a strong acid and in the absence of a base.

It has namely surprisingly been found that the hydrolysis of benzyl esters can be well effected under such mild reaction conditions, too.

The Journal of Supercritical Fluids, 1992, 5, 107–113 "Reactions of Supercritic Water with Benzaldehyde, Benzylidenebenzylamine, Benzylalcohol, and Benzoic acid", describes an experiment in which benzyl benzoate is hydrolyzed with $H_2O$ without a catalyst under supercritical conditions, i.e. at a very high pressure (26.7 MPa) and temperature (400° C.). These supercritical conditions however involve an extreme safety problem and moreover high investments, which is not desirable in commercial exploitation. Under these conditions water moreover behaves as an aggressive acid, as a result of which higher demands have to be imposed on the material of the equipment. Another drawback is the relatively poor selectivity owing to a relatively high degree of decomposition of benzyl alcohol and benzoic acid and hence the formation of undesired by-products.

EP-A-778257 also describes the hydrolysis of benzyl acetate with the aid of a strong acid ion exchanger as a catalyst. The life of such ion exchangers depends on the purity of the fraction to be hydrolyzed. In practice they are usually deactivated by cationic impurities even occurring in a low concentration. The temperature is moreover a limiting parameter in such a process. A cosolvent, for example acetone, is moreover required for the hydrolysis of higher benzyl esters, for example benzyl benzoate, to turn the benzyl benzoate/water system into a homogeneous phase. However, the use of a cosolvent is economically unattractive because it must in turn be separated from the ultimate product. As a result, extra process steps are required, which of course imply extra investments.

Examples of benzyl esters that are suitable for use in the process of the present invention are benzyl esters of organic carboxylic acids, for example benzyl formiate, benzyl acetate, benzyl propionate and benzyl benzoate.

Such benzyl esters are formed for example during the oxidation of monoalkylbenzene compounds, for example toluene, with molecular oxygen. The oxidation of toluene can take place either in the liquid phase or in the gas phase. In practice the resultant reaction mixture often contains benzoic acid; by-products with boiling points lower than that of benzoic acid, for example benzyl alcohol, benzaldehyde and light benzyl esters such as benzyl formiate, benzyl propionate and benzyl acetate; and products with boiling points higher than that of benzoic acid, such as benzyl benzoate, which are summarized under the heading tar residue. After recovery of benzoic acid and upgrading of the reaction mixture a tar containing benzyl benzoate often remains, which may still contain benzoic acid and/or a fraction with a boiling point lower than that of benzoic acid, which, in addition to benzoic acid, contains light benzyl esters such as benzyl formiate, benzyl propionate and benzyl acetate. Both the tar containing benzyl benzoate and the light fraction can be used as a starting material for the process according to the invention.

The hydrolysis of benzyl esters proceeds according to an equilibrium reaction. Because the hydrolysis reaction can be performed with a high degree of conversion of the benzyl ester, for example a degree of conversion of more than 90%, preferably more than 98%, for example via a favourable ratio of reactants or the removal of reaction product, a process stream can be obtained from which very pure benzyl alcohol can be recovered in a simple manner.

The benzyl ester/water molar ratio may vary within a wide range, for example between 50:1 and 1:500. Preferably the molar ratio varies between 1:1 and 1:200, in particular between 1:10 and 1:100.

The temperature and the pressure at which the hydrolysis reaction takes place may vary within a wide range. The temperature may for example vary from 40° C. to 320° C., preferably 80° to 300°. When the aim is the hydrolysis of higher benzyl esters, for example benzyl benzoate, a temperature higher than 150° C., for example between 180° and 320° C., in particular between 220° and 300° C., is preferably chosen. The autogenous pressure is preferably used as the pressure at which the hydrolysis reaction takes place. The pressure for example varies between 0.1 and 10 MPa, preferably between 1 and 10 MPa, in particular between 2 and 8 MPa.

The hydrolysis reaction according to the invention can be carried out in different types of reactors, for example a batch reactor, a plug-flow reactor, a continuously stirred tank reactor or combinations of different reactors.

The residence time in the reactor depends strongly on the type of reactor, the temperature and the corresponding pressure, the miscibility and degree of mixing of the system, the water/benzyl esters molar ratio and the composition of the feed. The residence time in the reactor may vary within a wide range, depending on the parameters chosen, for example between 1 minute and 10 hours, preferably between 2 minutes and 2 hours, in particular between 5 and 60 minutes. A person skilled in the art will be able to determine the optimum residence time in a simple manner on the basis of the desired degree of conversion of benzyl esters and the selectivity to benzyl alcohol.

A weak acid, for example an acid with a $pK_a$ of more than 3 and less than 7, may optionally be used in the hydrolysis reaction according to the invention. The determination of $pK_a$ used here is described in the 'Handbook of Chemistry and Physics', 60th ed. D 155–167. Preferably an acid formed during the hydrolysis reaction is added, for example formic acid, acetic acid, propionic acid or benzoic acid. In the hydrolysis the acid that corresponds to the acid residue of the benzyl ester is preferably added. As a result of this the reaction rate increases. The amount of acid to be added is not particularly critical. A person skilled in the art will be able to determine the optimum amount of acid to be added in a simple manner on the basis of the desired reaction rate, homogeneity of the system and the desired degree of conversion. The acid can be added at any moment, preferably at the beginning of the hydrolysis reaction. Preferably the amount of acid used and the chosen reaction conditions, for example the temperature, are controlled so that a homogeneous phase is obtained at the end of the hydrolysis.

The process according to the invention is particularly suitable for upgrading a tar containing benzyl benzoate. It results in conversion of the benzyl benzoate, which has a high boiling point and which is difficult to separate from certain tar components through distillation, into benzyl alcohol and benzoic acid, which have much lower boiling points and can easily be separated from one another. The benzyl benzoate is as such hydrolyzed in a simple manner to form the valuable and easily recoverable components benzyl alcohol and benzoic acid.

After the hydrolysis reaction the reaction mixture obtained is cooled and upgraded. The cooling can be effected for example by means of an external heat exchanger.

Cooling is for example effected to a temperature between 60° C. and 200° C., preferably between 80° C. and 180° C., in particular to a temperature between 100° C. and 160° C. The cooling causes phase separation, resulting in an organic phase and an aqueous phase. The organic phase is upgraded separately. An important advantage of this is that the relatively large amount of water does not have to be distilled.

During or after cooling an apolar solvent, for instance a hydrocarbon, specifically toluene, benzene or pentane may be added, if desired. Preferably toluene is added. An advantage of this measure is that the organic phase contains less water. From the organic phase, which contains predominantly benzoic acid and benzyl alcohol and optionally benzyl benzoate, tar and by-products with high boiling points, for example dibenzyl ether, the benzyl alcohol can subsequently be recovered in a simple manner using techniques known to a person skilled in the art, for example extraction or distillation; preferably the benzyl alcohol is recovered via distillation. The benzyl benzoate that has not reacted and the dibenzyl ether by-product can for example be returned to the reactor, both the benzyl benzoate and the dibenzyl ether being hydrolyzed to form benzyl alcohol and/or benzoic acid. This results in a high overall yield. The benzoic acid can be shaped as such or it can optionally be converted into sodium benzoate or phenol. The aqueous phase can optionally be returned to the reactor or it can be upgraded, from which the possibly valuable products such as benzoic acid or benzyl alcohol can be recovered for example after extraction.

With the process according to the invention benzyl alcohol can be obtained that has a purity of more than 95%, preferably more than 98%, in particular more than 99%. Benzyl alcohol is a useful product that is for example used in the fragrances and flavours industries. With the process according to the invention a hitherto unusable tar is consequently converted into useful substances.

The invention will be further elucidated with reference to the examples, without however being limited thereby.

EXAMPLES

Definitions of the abbreviations used in the examples;
Benzyl benzoate: BBZ
Benzyl alcohol: BA
Dibenzyl ether: DBE
2-, 3-, or 4-benzylbenzyl alcohol: BBA
selectivity to benzyl alcohol: $S_{BA}$
selectivity to dibenzyl ether: $S_{DBE}$
selectivity to benzylbenzyl alcohol: $S_{BBA}$
benzyl formiate: Bfor
benzyl acetate: BAc Example I 162 grams of BBZ was introduced into a Parr autoclave (volume 300 ml) fitted with a standard Rushton turbine mixer (1000 rpm). In 1 hour the autoclave was heated in a nitrogen atmosphere to a temperature of 240° C., after which 50 grams of water (temperature 240° C., pressure 4 MPa) was added with the aid of a side ampoule (t=0). The reaction mixture thus obtained was stirred for 4 hours at this temperature. Samples were taken of the reacting system after 1, 2 and 4 hours, which were analyzed with the aid of GLC.
after 1 hour:
    degree of conversion of BBZ: 5.4 mole %
    selectivity to BA: 99 mole %
    selectivity to DBE: 1 mole %
after 2 hours:
    degree of conversion of BBZ: 16.5 mole %
    selectivity to BA: 95 mole %
    selectivity to DBE: 3 mole %
    selectivity to BBA: 2 mole %
After 4 hours:
    degree of conversion of BBZ: 52.0%
    selectivity to BA: 90 mole %
    selectivity to DBE: 6 mole %
    selectivity to BBA: 4 mole %

Example II 76 grams of BBZ and 19 grams of benzoic acid were introduced into a Parr autoclave fitted with a standard Rushton turbine mixer (1000 rpm). In 1 hour the autoclave was heated in a nitrogen atmosphere to a temperature of 240° C., after which 150 grams of water (temperature 240° C., pressure 4 MPa) was added with the aid of a side ampoule (t=0). The reaction mixture thus obtained was stirred at this temperature. After 30 minutes a sample was taken of the reacting system, which was analyzed with the aid of GLC:
degree of conversion of BBZ: 60.0%;
selectivity to BA: 83 mole %
selectivity to DBE: 10 mole %
selectivity to BBA: 7 mole %.

Example III 715 grams of water, 167 grams of benzoic acid, 31.5 grams of diphenyl ether (as an internal standard for GLC analysis) and 488 grams of BBZ were at room temperature introduced into a Buchi autoclave fitted with 4 sight glasses (volume 2000 ml) and a standard Rushton turbine mixer (1000 rpm). The autoclave was inertized with nitrogen, after which the system was brought to a pressure of 0.3 MPa. In 2 hours it was heated (at 80° C. all the solids had dissolved and two separate liquid phases were visible) to a temperature of 220° C. (t=0, p=2.4 MPa), which produced a homogeneous liquid phase. This was followed by 2 hours' stirring (1000 rpm) at 220° C., which yielded a degree of BBZ conversion of 67.5% (selectivity to BA: 85 mole %, selectivity to DBE: 9 mole %, selectivity to BBA: 6 mole %). Next, the system was in 15 minutes cooled to a temperature of 180° C. (at 200° C. the homogeneous liquid phase separated into two separate phases: the supernatant aqueous liquid phase was clear (colourless); the bottom liquid phase was pale yellow); the two liquid phases were then analyzed with the aid of GLC.

|  | organic phase | water phase |
|---|---|---|
| benzyl alcohol: | 15 wt. % | 3.2 wt. % |
| benzyl benzoate: | 18 wt. % | 1.5 wt. % |
| benzoic acid: | 39 wt. % | 6.9 wt. % |
| diphenyl ether: | 3.7 wt. % | 0.2 wt. % |
| dibenzyl ether: | 1.7 wt. % | 0.15 wt. % |
| benzylbenzyl alcohol: | 1.1 wt. % | <0.1 wt. % |
| water | 20 wt. % | 88 wt. % |

Examples IV–VII

BBZ and water were fed to a continuous-flow stirred tank reactor (CSTR, liquid volume 200 ml) fitted with a standard Rushton turbine mixer (1000 rpm) at a certain temperature and pressure. Then a residence time of a few minutes was realized. The homogeneous reaction mixture thus obtained was subsequently cooled to a temperature of 95° C., which resulted in phase separation and the formation of an aqueous phase and an organic phase. The organic phase was analyzed with the aid of GLC.
The following were determined:
Degree of conversion of BBZ
selectivity to BA
selectivity to DBE
selectivity to BBA
The result is presented in Table 1.

TABLE 1

| Example | T [° C.] | BBZ [ml/min] | H$_2$O [ml/min] | time [min.] | P [MPa] | Degree of conv. of BBZ [mole %] | S$_{BA}$ [mole %] | S$_{DBE}$ [mole %] | S$_{BBA}$ [mole %] |
|---|---|---|---|---|---|---|---|---|---|
| IV | 250 | 2.5 | 2.5 | 40 | 5 | 48.7 | 83 | 12 | 5 |
| V | 270 | 5 | 15 | 10 | 6.8 | 68.9 | 83 | 8 | 9 |
| VI | 230 | 2.5 | 7.5 | 20 | 5 | 13.9 | 94 | 5 | 1 |
| VII | 250 | 3.3 | 10.0 | 15 | 5 | 48.7 | 85 | 8 | 7 |

Example VIII

A Parr autoclave (volume 300 ml) fitted with a standard Rushton turbine mixer (1000 rpm) was charged with 152 grams of a mixture of benzyl esters having the following composition: 5 wt. % Bfor, 5 wt. % BAc, 5 wt. % BA, 10 wt. % 2-methyl diphenyl (as an internal standard for GLC analysis), 5 wt. % benzaldehyde and 70 wt. % benzoic acid. In 30 minutes the autoclave was in a nitrogen atmosphere heated to a temperature of 120° C., after which 38 grams of water (temperature 120° C., pressure 4 MPa) was added with the aid of a side ampoule (t=0). The reaction mixture thus obtained was stirred at this temperature for 2 hours. After 2 hours samples were taken of the reacting system, which were analyzed with the aid of GLC.
Degree of conversion of Bfor: 85 mole %
Degree of conversion of BAc: 25 mole %
The mixture contained 0 wt. % dibenzyl ether and 9 wt. % benzyl alcohol.

Example IX 100 g of a mixture of benzyl esters having the same composition as in Example VIII was introduced into a Parr autoclave fitted with a standard Rushton turbine mixer (1000 rpm). In 1 hour the autoclave was heated in a nitrogen atmosphere to a temperature of 240° C., after which 100 grams of water (temperature 240° C., pressure 4 MPa) was added with the aid of a side ampoule (t=0). The reaction mixture thus obtained was stirred at this temperature for 2 hours. After 2 hours a sample was taken of the reacting system, which was analyzed with the aid of GLC:
degree of conversion of Bfor: 99 mole %;
degree of conversion of BAc: 95 mole %
The mixture contained 1 wt. % dibenzyl ether and 11 wt. % benzyl alcohol.

Example X 100 grams of tar residue was introduced into a Parr autoclave fitted with a standard Rushton turbine mixer (1000 rpm). The tar residue contained 20 wt. % benzoic acid, 40 wt. % benzyl benzoate and 30 wt. % unknown tar components with high boiling points (boiling points>300° C.). In 1 hour the autoclave was heated in a nitrogen atmosphere to a temperature of 240° C., after which loo grams of water (temperature 240° C., pressure 4 MPa) was added with the aid of a side ampoule (t=0). The reaction mixture thus obtained was stirred at this temperature for 1 hour. After 1 hour a sample was taken of the reacting system, which was analyzed with the aid of GLC:
degree of conversion of BBZ: 62 mole %;
selectivity to BA: 85 mole %
selectivity to DBE: 8 mole %
selectivity to BBA: 7 mole %.

What is claimed is:

1. A process for the preparation of benzyl alcohol from a tar containing benzyl benzoate formed during oxidation of a monoalkylbenzene compound, the process comprising:
   hydrolyzing the tar containing benzyl benzoate in the absence of a strong acid and in the absence of a base at a temperature between 40° C. and 320° C. and a pressure between 0.1 MPa and 10 MPa, for a reaction time between 1 minute and 10 hours.

2. The process according to claim 1, wherein the hydrolysis takes place at a temperature higher than 150° C.

3. The process according to claim 1, characterized in that an acid with a pk$_a$ of more than 3 is added to the reaction mixture.

4. A process according to claim 3, wherein the acid is a member selected from the group consisting of benzoic acid, formic acid, propionic acid and acetic acid.

5. The process according to claim 4, wherein benzoic acid is added to the reaction mixture.

6. The process according to claim 1, characterized in that the benzyl benzoate/water molar ratio lies between 50:1 and 1:500.

7. The process according to claim 6, wherein the benzyl benzoate/water molar ratio lies between 1:10 and 1:100.

8. The process according to any claim 1, wherein the reaction mixture is cooled after the hydrolysis.

9. The process according to claim 8, wherein after hydrolysis the reaction mixture is cooled to a temperature of between 80° C. and 180° C., which causes a phase separation, resulting in an organic and an aqueous phase.

10. The process according to claim 9, wherein the organic phase is upgraded via distillation.

11. The process according to claim 9 or claim 10, wherein the aqueous phase is upgraded via extraction.

12. The process according to claim 10, wherein the benzyl benzoate and dibenzyl ether are returned to a reactor after the hydrolysis.

13. The process according to claim 1, wherein benzyl alcohol is obtained by means of a hydrolysis reaction with a degree of conversion of >98%.

14. The process according to claim 1, wherein benzyl alcohol with a purity of more than 98% is obtained.

15. The process according to claim 1, wherein the tar comprises about 40 wt. % benzyl benzoate.

* * * * *

UNITED STATES PATENT AND TRADEMARK OFFICE
CERTIFICATE OF CORRECTION

| | | |
|---|---|---|
| PATENT NO. | : 6,326,521 B2 | Page 1 of 1 |
| DATED | : December 4, 2001 | |
| INVENTOR(S) | : Van Soolingen et al. | |

It is certified that error appears in the above-identified patent and that said Letters Patent is hereby corrected as shown below:

<u>Title page,</u>
Item [30], insert:
-- [30]    Foreign Application Priority Data

Dec. 18, 1997   the Netherlands ................. 1007829 --

Signed and Sealed this

Seventeenth Day of September, 2002

Attest:

Attesting Officer

JAMES E. ROGAN
*Director of the United States Patent and Trademark Office*